United States Patent [19]
Cabrera

[11] 4,152,391
[45] May 1, 1979

[54] LIQUID TRANSFER VALVE

[75] Inventor: Pedro P. Cabrera, Miami, Fla.

[73] Assignee: Coulter Electronics, Inc., Hialeah, Fla.

[21] Appl. No.: 861,356

[22] Filed: Dec. 16, 1977

[51] Int. Cl.$^2$ .............................................. G01N 1/14
[52] U.S. Cl. ................................. 422/103; 73/422 R
[58] Field of Search .......................... 23/259, 253 R; 73/422 R

[56] References Cited

U.S. PATENT DOCUMENTS

| | | | |
|---|---|---|---|
| 3,567,389 | 3/1971 | Coulter et al. | 23/259 X |
| 3,567,390 | 3/1971 | Rothermel | 23/259 X |
| 3,652,228 | 3/1972 | Bernard | 23/253 R |
| 3,976,429 | 8/1976 | Ginsberg | 23/259 |
| 3,990,853 | 11/1976 | Godin | 73/422 R X |
| 3,991,055 | 11/1976 | Godin et al. | 23/259 |

*Primary Examiner*—R. E. Serwin
*Attorney, Agent, or Firm*—Silverman, Cass & Singer, Ltd.

[57] ABSTRACT

A liquid transfer valve assembly capable of measuring and transferring plural different volumes from a sample source to defined flow paths under the influence of pressurized fluid. The preferred valve assembly includes a pair of stationary outer disc members and a movable inner disc member sandwiched therebetween, their facing surfaces sealingly frictionally engaged. Each of the discs has a central axial passage arranged for mounting on a spindle, with the sandwiched disc having a radial pin entering its axial passage for cooperation with a slotted spindle, the rotation of the spindle rotating only said sandwiched disc relative between a pair of positions. The center disc carries at least a segmenting bore pair, at least one of the bores being a measuring passage and having a precise volume. A matching port pair is provided in each of the outer discs defining flow paths through the valve arranged selectively to be intercepted by said measuring bore of the segmenting bore pair. The center disc also carries at least one exterior sample loop sealingly fixedly secured thereto and communicating to passageways formed in the disc. A flow path also is defined in said center disc to communicate to the face of said disc opposite to the face from which the exterior sample loop extends, said flow path may take the form of an internal passageway formed interior of the center disc and opening to said opposite face, or, may take the form of a groove. Plural sets of ports are formed in one of the outer discs to establish flow paths communicating to the hollow loop member in one position of the valve and to the flow path in the other condition of the valve. The other outer disc includes a generally arcuate slot for accommodating the sample loop therethrough in assembled condition of the valve, the slot being generally arcuate but including a flat wall portion to accommodate the hollow loop during the movement thereof with movement of the center disc. The center disc is provided with a circumferential notch cooperating with a mounting post to limit the extent of movement of said disc between positions. Proper establishment of the respective flow paths in the two operating positions of the valve is assured. A second external hollow loop is described and is associated with a further flow path in the center disc. Likewise, associated port sets are formed in said other outer disc to establish communication to said second sample loop in one condition of the valve. Each of the loops are of precise internal volume; each serving to measure and to transfer its liquid segment of precise volume to a selected destination. The said further flow path is established as a gallery in the form of an arcuate groove.

15 Claims, 8 Drawing Figures

LIQUID TRANSFER VALVE

INCORPORATION BY REFERENCE OF CERTAIN RELATED PATENTS

This invention is directed to improvements in liquid transfer valves for use in a diluting system and of the general type disclosed in U.S. Pat. Nos. 3,567,590 and 3,991,055 respectively, granted Mar. 2, 1971 and Nov. 9, 1976 for use in systems of the type described in U.S. Pat. No. 3,549,994.

Each one of these three identified patents is hereby incorporated by reference into this application and made a part thereof so that reference may be made thereto for the background and functional operations of the diluting systems and valve assemblies disclosed therein which are employed in such systems.

Each of these patents is owned by the assignee of this application.

FIELD OF THE INVENTION

This invention relates generally to liquid transfer systems and more particularly provides a liquid transfer valve of the rotary operating type capable of being substituted for the linearly operating spool type valve disclosed in the referenced U.S. Pat. No. 3,991,055 in the diluting system therein disclosed.

The fluid transfer valve of the referenced U.S. Pat. No. 3,991,055 enabled the delivery of at least two different volumes of a single sample along with the same amount of diluent to two different locations simultaneously so that tests could be performed upon said resultant dilutions at said locations at the same time. The referenced valve also enabled the operator to elect operation either upon a single whole blood sample or upon a prediluted sample without using separate valving, fluid lines, etc.

The said patented valve was a linearly movable so-called spool valve which is expensive both to construct and to maintain.

Accordingly, it would be advantageous to provide a valve construction which could be substituted for said spool valve and be capable of effecting all the operational functions of said spool valve and yet be less costly to manufacture and to maintain.

The desired valve assembly should be of compact construction and assembly, easy to dismantle and clean during maintenance and easy to reassemble.

SUMMARY OF THE INVENTION

Accordingly, the liquid transfer valve of the invention can be described as having internal segmenting passageway means and at least one external hollow loop of precise internal volume thereby to provide the different volumetric amounts of a liquid sample for dilution, each directed with a common amount of diluent at the same time to different predetermined locations. An additional external loop is provided, if desired, to give the same valve assembly the capability for dealing with a prediluted sample to be directed first to a first testing apparatus and next, as a segmented portion with a given amount of diluent to a second testing apparatus. Means are provided to accomplish rinsing (backwashing) with diluent during the delivery condition of the valve.

More specifically, the invention provides a liquid transfer valve assembly comprising a movable central member and a pair of stationary outer members engaged sealingly, frictionally against opposite faces of said central member to sandwich same therebetween. The central member is movable rotationally (angularly) between first and second positions, at least one pair of parallel through bores formed in said central member, at least one of said pair having a precise measuring volume. At least a pair of first ports are formed in each of said outer members so that the first ports in one outer member align with the first ports in the other outer member defining a first set of fluid flow paths. The central member is capable of being indexed to a first position whereat said one through bore intercepts one of said set of fluid flow paths to entertain a portion of liquid flowing in said one flow path. The central member is indexed to a second position whereat said one bore segments and transfers the entrained liquid portion therewithin to the other one of said first fluid flow path set for delivery to a predetermined location. Port means are provided in the other of said outer members defining a second set of fluid flow paths through only the other outer members, and the central member. The second flow path includes an external hollow loop extending outward of said central member and having a precise internal volume. The external hollow loop is rotatably translated with said central member simultaneously with the indexing of said member whereby to subtend and transfer a precise entrained second volume of liquid within the loop from one of said second liquid flow path set to the other of said set for delivery to a second predetermined location.

The invention also may provide third port means to define a third set of flow paths similar to said second set of flow paths but including a second external hollow loop of different volume. The third set of flow paths include an internal gallery formed as a groove or recess in the face of the central member engaged with said one outer member. The second hollow loop has its ends sealing coupled to the central member and extends in the direction substantially parallel to said first hollow loop, suitable slot means being formed in said one outer member to accommodate said second loop enabling rotation of the center member.

Preferably, the invention is embodied in a structure wherein said central and outer members are in the form of discs coaxially mounted with their facing surfaces sealing engaged frictionally, one of said discs serving as said other outer member and the other of said outer discs having said slot means; suitable notch means and/or said slot means defining the limits of angular movement required to establish said first and second positions of said valve.

DESCRIPTION OF THE DRAWINGS

FIG. 3 is a plan view of one outer member of the valve assembly of FIG. 2 and FIG. 3A is a plan view of the opposite face of said one outer member;

FIG. 4 is a plan view of the central member of the valve assembly of FIG. 2 and FIG. 4A is a plan view of the opposite face of said central member, the loops being shown in phantom line in FIG. 4; and FIG. 5 is a plan view of the other outer member of FIG. 2, and FIG. 5A is a plan view of the opposite face of said other outer member.

DESCRIPTION OF PREFERRED EMBODIMENTS

Generally, the liquid transfer valve according to the invention as will be described hereinafter is capable of delivering from a single sample, at least two different volume segments simultaneously for dilution with diluent. Means are provided for establishing at least two sets of fluid flow paths selectively traversed by at least a pair of different precise measuring sections, one of said pair being defined by an internally located segmenting bore set and the other of said pair being defined as including the internal volume of an external hollow loop.

A known volume is selectively segmented, that is, received and isolated from each of said pairs of paths and delivered to the associated other of said pairs of paths. The same given volume of diluent is introduced to each of the other of said path pairs so that the dilutions delivered from said measuring sections are determined by the volume of said measuring sections. Means are provided generally in the form of internal galleries to enable rinsing of the first path simultaneously with the delivery of the dilutions from the valve into the second path. An independent measuring section is defined including a second external hollow loop, and cooperates with another set of fluid flow paths whereby to enable the valve to receive, isolate and deliver a different dilution to a predetermined location, the source of said isolated dilution thereof being a prediluted volume of sample. The prediluted sample is directly fed directly along one path to one testing path apparatus at the first position of the valve and the subtended volume, i.e., including the internal volume of the second external loop, is delivered to the second testing apparatus at the second position of the valve.

Figure 1:
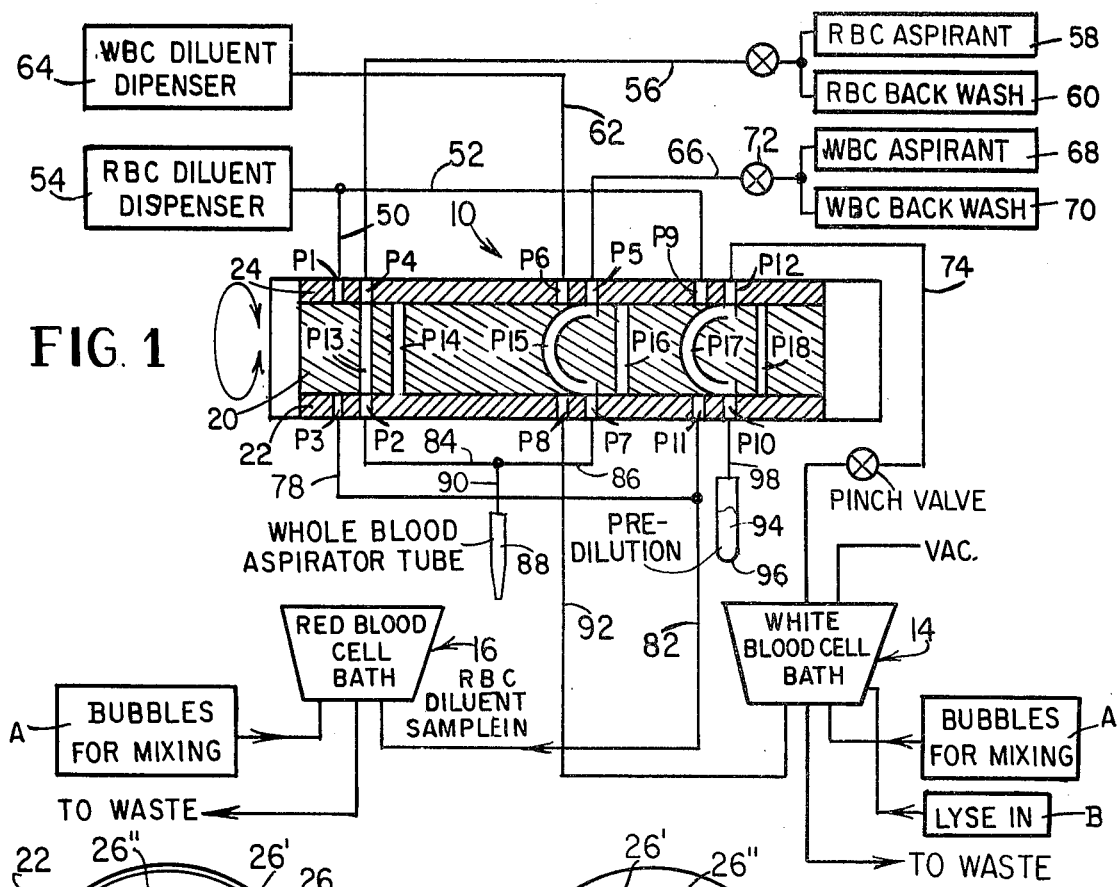
FIG. 1 is a diagrammatic representation illustrating the general operation of the liquid transfer valve constructed in accordance with the invention as employed in a diluting system supplying a testing apparatus.

Referring to the drawings, a diagrammatic representation illustrating the general operation of the liquid transfer valve constructed in accordance with the invention in a diluting and testing system is illustrated in FIG. 1. This system is substantially the same as the system illustrated in FIG. 1 of U.S. Pat. No. 3,991,055. However, the passageway P15 of the patented valve is in the form of an external loop. Passageway P16 of the patented valve is in the form of a gallery preferably formed as an internal passageway within the center member of the valve. Ports P5 and P7 are formed in only one outer member of the valve, as are formed port pairs P6 and P8.

Likewise, passageway P17 is in the form of a second external loop while passageway P18 is in the form of an internal gallery preferably taking the form of a groove formed in a face of the central valve member. The Functional operation and cooperation of the respective passageway and port pairs, etc. of the valve disclosed herein are substantially the same as the functional operation and cooperation illustrated and described in said U.S. Pat. No. 3,991,055, and reference may be made to said patent for additional description thereof.

The general system for fluid handling is connected with testing apparatus operating in accordance with the principle taught in U.S. Pat. No. 2,656,508 for the determination of various parameters of blood cell characteristics. A first apparatus is indicated generally by block 14 and a second testing apparatus is represented generally by block 16. Actual dilution, that is, mixing and adding of reagents when necessary, is performed in one vessel of each testing apparatus 14 and 16. The fluid transfer valve according to the invention is coupled to the aforesaid apparatus by fluid lines which will be described hereinafter in connection with the operation of the subject valve.

For ease in description, the representation of the liquid transfer valve 10 in respect of the relationship of the various passageways, bores, etc. during operation will be described diagrammatically in terms of a linear representation although the valve is formed as an assembly wherein a central, here rotatably movable valve element 20 is formed as a disc sandwiched between a pair of coaxially arranged outer stationary elements, discs 22, 24.

The stationary elements 22 and 24 are arranged apart only sufficiently to accommodate the thinner central element 20 therebetween.

The outer members 22, 24 are provided with faces 22' and 24' which are engaged with the opposite faces 20' and 20" of the central element 20. The faces 20', 20", 22' and 24' are machined carefully, stress relieved by heat treatment and coated with an acid resistant chromium oxide-aluminum oxide coating whereby wear effect is reduced, and friction effects binding, etc., also are reduced.

Each of the disc elements 20, 22 and 24 have a central passageway. The central or axial passageways formed in these elements 20, 22 and 24 are of the same diameter. The three elements are mounted coaxially on a slotted spindle, as will be described.

Figure 2:
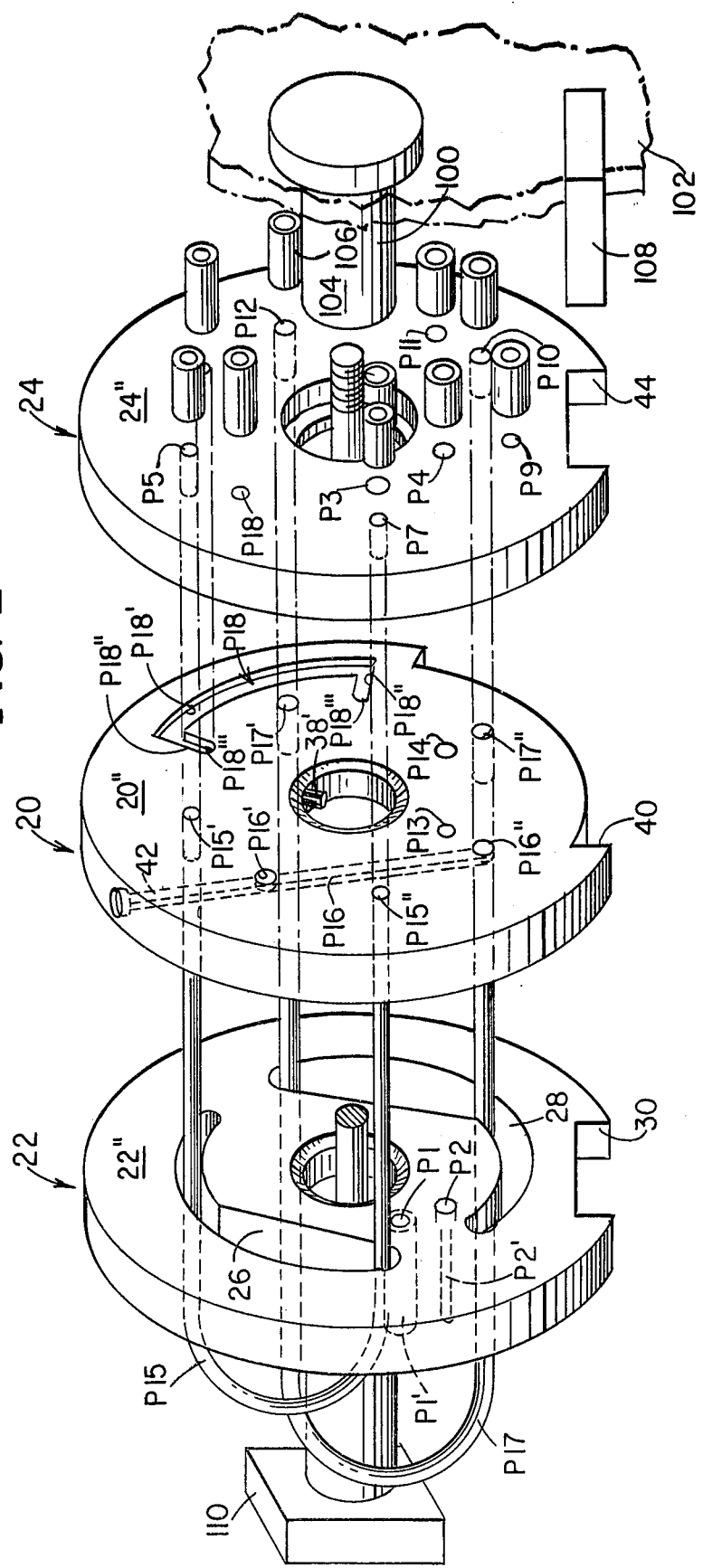
FIG. 2 is an isometric exploded and diagrammatic representation of the liquid transfer valve assembly constructed in accordance with the invention.

Referring to FIGS. 2, 3 and 3A, a pair of parallel axial passageways P1 and P2 are formed in outer disc 22. The axial centers of passageways P1 and P2 are spaced identical distances "a" from the center axis of said disc 22. The center axes of passageways P1 and P2 are spaced apart a distance "b." A pair of through slots 26 and 28 of generally arcuate configuration are formed in said disc 22. A circumferential notch 30 also is formed in disc 22. The outer walls 26' and 28' of the respective slots 26 and 28 lie along a circle which is concentric with the central passageway 32 of the disc 22 while only portions 26" and 28" of the inner walls of said slots 26 and 28 are arcuate and respectively lie along a circle concentric with said central passageway 32 with the remaining portions of said inner walls bridging the ends and said wall portions 26" and 28" of said slots lying along a straight line. Suitable fittings P1' and P2' are provided for seating on the disc 22 in communication with said passageways P1 and P2, same disposed extending from the face 22" of said disc 22.

Attention now is directed to the central element or disc 20. As illustrated in FIGS. 2, 4 and 4A, the disc 20 has a central axial passageway 34 formed therein. A radial bore 36 is formed in the central disc leading from the outer circumference of the disc 20 to the central passageway 34 thereof and a pin 38 is press-fitted therein with its innermost end 38' entering said passageway 34. The disc 20 carries a circumferential notch 40. Notch 40 has a considerable circumferential length greater than the length of notch 30 and like notch 44 formed on outer disc 24 for a purpose as will be described later.

A pair of parallel bores P13 and P14 are formed through disc 20 with their axial centers spaced identially a distance "a" from the center axis of the disc 20, and spaced from each other, a distance "b." Bore P14 has a slightly larger diameter than bore P13.

A pair of parallel through bores P15' and P15" are formed through disc 20, the center axes of said bores having their axial centers spaced a distance "c" from the axial center of said bores P15' and P15", same being spaced a distance "d" from each other. A hollow loop P15, in the form of a predetermined length of U-shaped hollow tubing, preferably formed of stainless steel, which has a uniform bore to define a uniform precise internal volume, is secured to the face 20' of disc 20 with the free ends thereof sealingly in communication with said bores P15' and P15".

A pair of shallow passageways P16' and P16" are formed in the disc 20 opening only to face 20" thereof. The center axes of said passageways P16' and P16" are spaced a distance "d" from each other and the said axial centers are spaced a distance "c" from the axial center of said disc 20. The center axis of passageway P15' is spaced a distance "e" from the center axis of passageway P16' while the center axis of passageway P15" is spaced the same distance "e" from the center axis of passageway P16".

A straight-line internal passageway P16 is formed in disc 20 leading from the circumferential surface of said disc 20 and communicating between the inner ends of passageways P16' and P16" linking the same. A plug 42 closes the passageway P16 from the circumference of the disc 20.

A third set of parallel passageway pairs P17' and P17" also are formed in said disc 20 with the center axes thereof being spaced radially from the center axis of disc 20 by distance "c." Passageway P17" is formed at a location diametrically opposite the location of passageway P15', while passageway P17' is formed at a location diametrically opposite the location of passageway P15".

An internal gallery P18 is defined within the valve 10 by the formation of an arcuate groove P18' in face 20" of disc 20, which groove has end extensions P18" leading radially inward to termini P18''', the ends of which are defined by a semi-cylindrical wall lying in a circle having a center point coincident with and lying upon a circle concentric with the center axis of the disc 20. The distance between the center to center points of said ends are the same as the distance between center axes of said passageways P17' and P17", the arc followed by the groove P18 lying along a circle concentric with center axis of disc 20. A second hollow loop P17 in the form of a length of uniform cross-section U-shaped hollow tubing, again preferably formed of stainless steel, and having a precise uniform internal volume is secured to the face 20' of disc 20 in sealed communication with said passageways P17' and P17". The second loop P17 has a greater internal diameter and a greater length than the first loop P15. Thus, the volume subtended by and within the confines of second loop P17 including portions of passageways P17' and P17" not occupied by the ends of loop P17, is different from, and preferably is greater than, the volume subtended by and within the confines of the first loop P15(also including portions of passageways P15' and P15" not occupied by the ends of the loop P15).

Referring to FIG. 2 and FIGS. 5 and 5A, the other outer disc 24 is provided with a face 24' also having an anti-friction, acid resistant coating thereupon identical to the coating provided on faces 20' and 20" as well as the coating carried by face 22" of outer member 24. Opposite face 24" has ports in the form of fittings to establish exterior communication to the valve 10 as will be described hereinafter.

A set of parallel through passageways P3 and P4 is formed in disc 24 at a location so that said passageways P3 and P4 are aligned with passageways P1 and P2 formed in disc 24 whereby to define a first set of flow paths through the valve. At the first position of the center disc, only the passageway P13, that is the measuring passageway communicates with the flow path defined by passageways P2 and P4, while in the second position of said center disc 20, the passageway P13 communicates with the flow path defined by aligned passageways P1 and P3, while the passageway P14 intercepts the flow path defined by aligned passageways P2 and P4.

A second set of parallel through passageways P5 and P7 is formed in disc 24 and a third set of like diameter parallel through passageways P6 and P8 also is formed in said disc 24. Passageway set P5 and P7 is located to communicate with the first loop P15 during the first position of the center disc 20 and to communicate with the internal passageway P16 during the second position of the center disc 20.

The second set of parallel passageways P5 and P7 defines a third flow path while the third set of parallel passageways P6 and P8 defines a fourth flow path. The first loop P15 thus communicates with the third flow path during the first or load position of the disc 20. The loop P15 communicates with the fourth flow path during the second or delivery position of the disc 20. Simultaneously with the establishment of communication between the first loop P15 and the fourth flow path, the internal passageway P16 is placed into communication with the third flow path.

A fourth set of parallel through passageways P9 and P11 is provided in the disc 24 and a fifth set of parallel through passageways P10 and P12 also is formed in said disc 24. The fourth set of passageways P9 and P11 establishes a fifth flow path. The fifth set of parallel passageways P10 and P12 establishes a sixth flow path. The fourth and fifth sets of through passageways are located in disc 24 so that the second sample loop P17 is in communication with the sixth flow path during the first position of the disc 20; and, when the disc is indexed to the second position, the sample loop P17 is placed in condition to enter the fifth flow path while the gallery P18 is placed into the sixth flow path. In view of the fact that the second loop P17, the gallery P18 and the fifth and sixth flow paths are employed only when the source of liquid sample is a prediluted sample, the first through fourth flow paths are not used when such prediluted sample source is used. The disc 24 has a circumferential notch 44.

As installed in the system represented diagrammatically in FIG. 1, there are fluid lines leading between the valve assembly 10 and the elements of the diluting as well as the testing system. Line 50 and 52 couple passageways P1 and P9 to a source 54 for dispensing a predetermined volume of diluent to said passageways P1 and P9. Fluid line 56 connects the passageway P4 with a source of vacuum 58 and a source of diluent 60 alternatively through suitable valve means. Line 62 connects passageway P6 with diluent dispenser means 64 for dispensing to passageway P6 of a given volume of diluent. Line 66 connects passageway P5 to a source of vacuum and a source of diluent alternatively, respectfully designated by reference characters 68 and 70 through suitable valve means 72. Line 74 connects passageway P12 with testing apparatus 14 through a suitable valve, here pinch valve 76.

Lines 78 and 80 connect passageways P3 and P11 respectively to line 82 which leads to testing apparatus 14. Lines 84 and 86 respectively connect passageways P2 and P7 with a whole blood aspirator 88 through line 90. Fluid line 92 couples passageway P8 to testing apparatus 14.

In the system illustrated, testing apparatus 14 provides white blood cell parameter determinations while testing apparatus 16 provides red blood cell parameter determinations. Suitable mixing bubbles are fed to the mixing vessel of apparatus 14 and 16 from a source A thereat while lysing solution is fed to apparatus 14 from a source B thereof. Suitable conduits lead from the respective testing apparatus 14 and 16 to waste.

As mentioned in the referenced patent and hereinabove, the valve 10 operates between two positions by angular movement of the center element, disc 20. The first position can be referred to as the loading position. Since loading is effected by coupling from a source 88 of sample through the valve 10 to a source of vacuum, the first position also can be described as an aspirating position. The delivery or dispensing is performed by feeding a given quantity of diluent to the valve passageways subsequent to rotation of the center element 20 to the second position which may be described as the dispensing or delivery position. In the delivery position, the volume of sample subtended interior of the segmenting passageway P13 and the first loop P15 is driven, respectively, to the testing apparatus 16 and testing apparatus 14. Either at the same time that the subtended segments are swept out or subsequently, diluent is introduced to rinse the pathways leading back to the source 88 of sample. The passageway P14 is aligned with passageways P2 and P4, while the internal passageway P16 is placed into communication with passageways P6 and P8 during rinsing.

Where the predilution sample source is used, the second loop P17 communicates with passageways P10 and P12. Prediluted sample 94 from container 96 is directed via line 98 to passageway P10 and, traveling through the second loop P17 to passageway P12, it is directed via line 74 and through pinch valve 76, to the testing apparatus 14. When the valve 10 is driven to its delivery position, i.e., the second position, the loop P17 is placed in communication with passageways P9 and P11, the subtended volume of prediluted sample within said loop P17 being placed into the flow path defined by the passageway P9, the loop P17 and the passageway P11, and by way of line 80 and 82 to testing apparatus 16. The remaining liquid content of vessel 96 is directed simultaneously or later to the testing apparatus 14 by way of gallery P18 from whence it is aspirated to waste, as indicated in FIG. 1.

In a practical example of the valve assembly 10, the linear distances between axial centers of the passageways formed in the associated valve elements were:
 a=0.406
 b=0.3304
 c=0.625
 d=0.752
 e=0.508
The liquid volume subtended:
 by passageway P13 was 1.6λ(microliters)
 by the loop P15 was 42.9λ(microliters) and
 by the loop P17 was 359.55λ(microliters)

The volume of diluent dispensed during delivery of each of the subtended volumes of sample comprises 10 cc. (isotonic water being used) to provide suitable dilutions for the tests to be conducted in apparatus 14 and apparatus 16.

The discs 20, 22 and 24 are supported by being strung out on spindle 100 which extends out of a stationary mounting plate 102. Spindle 100 is rotatable relative to the stationary mounting plate and includes a slotted end portion 104 carrying slot 106. The pin end 38' of pin 38 is engaged within the slot 106 so that rotation of the spindle rotates the disc 20 to index same between the first and second positions.

In addition to spindle 100, plate 102 carries a stationary rectangular block-like post member 108. When the three discs 20, 22 and 24 are strung on spindle 100, the post 108 is received through notches 30 and 42 so as to fix said discs against angular movement. As the central disc 20 is indexed, the post 108 rides in the long circumferential notch 40, the opposite ends of notch 40 cooperating with the post 108 to define the limits of rotation of disc 20.

The respective valve elements, discs 20, 22 and 24 are held in assembly on spindle 100 by bolt 110, the threaded end of which passes through spindle 100 and is engaged in or by a spring biased arrangement (not shown) on the opposite side of plate 102.

The spindle 100 may be rotated to index said disc 20 by an articulated linking pivot connection between the reciprocable plunger of a pneumatic cylinder and the spindle so that reciprocation of said plunger is translated into angular rotational movement of the spindle.

It should be apparent that when the valve 10 is in assembled and operating condition, the loops P15 and P17 pass through and move within slots 26 and 28 respectively.

Although in the aforesaid description, the valving portions utilizing the small volume segmenting passage P13 and the intermediate volume loop P15 are not utilized when the predilution loop P17 is used, the couplings and fluid flow conduits and connections may be adjusted so as to enable use of the substantially larger volume predilution loop P17 in conjunction with the segmenting operating of the small volume segmenting passage P13. Any one of passage P13, loop P15 and/or loop P17 can be used independently of the others or in cooperation with one or the other or both of the others.

It is believed apparent that much variation and substitution of equivalents are capable of being made without in any way departing from the spirit and scope of the invention as defined in the appended claims.

What I claim is:

1. A liquid transfer valve for use in a diluting system for providing at least a pair of different segmented samples from a source thereof, the volume of one segmented sample being different than the volume of the other segmented sample of said pair, and in which said transfer valve has a first portion for receiving and isolating therein an amount of liquid sample and for combining said amount of sample with a first volume of a diluent to produce a precise desired first dilution, a second transfer valve portion for receiving and isolating therein a different amount of liquid sample and for combining said amount of sample with the same quantity of diluent to produce a second dilution, said first transfer valve portion comprising segmenting passageway means formed interior of sad valve and said second transfer valve portion comprising an external hollow loop member of precise internal volume.

2. The liquid transfer valve as claimed in claim 1 in which said transfer valve is defined by a pair of outer valve elements spaced apart and an inner valve element sandwiched between said outer valve elements and having opposite faces sealingly frictionally movable engaged with adjacent faces of said outer valve elements, said inner valve element being movable angularly to place said first and second valve portions in loading and delivery positions, said internal segmenting passageway means formed in said inner valve element and said external loop member secured to one face of said inner valve element, said other of said outer elements adjacent said one face having slot means for accommodating said loop member therethrough during movement of said inner valve member while enabling maintenance of frictional engagement of said inner valve element with said outer valve elements.

3. The liquid transfer valve as claimed in claim 2 wherein there is a third transfer valve portion for receiving and isolating a third amount of liquid sample from a source thereof and for combining said third amount with a given volume of diluent to produce another dilution, said third valve portion comprising a second external hollow loop member having a precise internal volume different from the internal volume of said first hollow loop member.

4. The liquid transfer valve as claimed in claim 3 in which said last mentioned source is a prediluted liquid sample.

5. The liquid transfer valve as claimed in claim 1 and internal gallery means capable of being communicatively coupled to a source of diluent for rinsing the valve portions.

6. The liquid transfer valve as claimed in claim 5 in which said internal gallery means includes means defining at least one internal passageway capable of being communicatively coupled to said transfer valve portions during rinsing.

7. The liquid transfer valve as claimed in claim 5 in which said internal gallery means includes groove means formed in the other face of said inner valve element and capable of being communicatively coupled to said second transfer valve portion during rinsing.

8. The liquid transfer valve as claimed in claim 5 in which said internal gallery means includes means defining at least one internal passageway capable of being communicatively coupled to at least one of said first and second transfer valve portions and groove means formed in the other face of said inner valve element and being capable of being coupled communicatively to said third transfer valve portion during rinsing.

9. A liquid transfer valve for use in a diluting system for providing at least a pair of different segmented liquid samples from a single source thereof, the volume of one segmented sample being different than the volume of the other segmented sample of said pair, said transfer valve having a first valving portion for receiving and isolating therein a predetermined amount of the liquid sample and for combining said amount of sample with a first volume of diluent to produce a precise desired first dilution, a second valving portion for receiving and isolating therein a different amount of said sample and for combining said amount with the same quantity of diluent to produce a precise desired second dilution, said transfer valve comprising an assembly formed of a pair of outer stationary disc members and a movable central disc member, each of said disc members having a central axial passageway, said disc members being assembled coaxially aligned with said outer disc members being engaged against the opposite faces of said central disc member in fluid tight, frictional relationship, means for limiting movement of said central disc relative to said outer stationary disc members to a predetermined arc with the terminal locations at the ends of said arc defining first and second positions of said central disc member, said central member having at least a pair of parallel through first bores formed therein and said outer members each having a pair of matching aligned ports formed therethrough, at least one of said bores having a precise internal volume and together defining said first valving portion, said central disc having at least two additional pair of parallel passageways, a first hollow loop member having a pair of free open ends seated sealingly into one face of said central disc communicatively entering into openings of one of said pair of second passageways, slot means formed in that one of said outer disc members which is adjacent said one face to enable passage of said first loop therethrough and to enable angular movement of said first loop with movement of said central disc member along said predetermined arc, means formed in said central disc member defining an internal flow path communicating between said other of said pair of second passageways, at least two pair of second ports formed in the other of said outer disc members, one pair of said second port pairs arranged to be coupled communicatively to the ends of said first hollow loop in the first position of said central disc member and the other pair of said second port pairs arranged to be communicatively coupled to the ends of said first loop in the second position of said central disc member, said first loop having a predetermined precise internal volume and included in said second transfer valve portion, said first and second transfer valve portions capable of having liquid sample introduced thereinto simultaneously and of delivering the same also simultaneously while directing diluent into the other bore, the internal flow path, and ports respectively associated therewith for rinsing the path defined thereby.

10. The liquid transfer valve assembly as claimed in claim 9 in which said means defining an internal flow path comprise an internal passageway formed in said central disc and opening to said other face of said central disc.

11. The liquid transfer valve assembly as claimed in claim 9 in whch said means defining an internal flow path comprise groove means formed in said other face of said central disc, said one of said second passageway pairs being through passageways and said other of said passageway pairs being terminal extensions of said groove means opening only to said other face.

12. The liquid transfer valve assembly as claimed in claim 9 in which there are at least an additional two pair of passageways formed in said central disc and a second hollow loop member having open free ends seated into the said one face of said central disc member sealingly in communication with one pair of said additional two pair of passageways, said other outer disc member having additional port pairs, one pair of which arranged to communicate with said second hollow loop in the first position of the central disc and the other pair of which to communicate with said second hollow loop in the second position of said central disc, and means defining an internal flow path associated with said other of said second passageway pairs and capable of communicating with the said one pair of said additional port pairs in the second position of said central disc member, said second hollow loop member having a precise internal volume.

13. The liquid transfer valve assembly as claimed in claim 12 in which said second hollow loop member has an internal volume different from the internal volume of said first hollow loop member.

14. The liquid transfer valve assembly as claimed in claim 12 in which said second hollow loop member has an internal volume greater than the internal volume of the first hollow loop member.

15. The liquid transfer valve assembly as claimed in claim 12 in which said means defining a flow path between said other of said additional passageway pairs comprise groove means formed in said other face of said central disc member linking said other of said additional passageway pairs and said last mentioned additional passageway pair being terminal extensions of said groove means opening only to said other face.

* * * * *